(12) United States Patent
Naito et al.

(10) Patent No.: US 9,448,241 B2
(45) Date of Patent: Sep. 20, 2016

(54) MASS SPECTROMETRY METHOD FOR A POLYPEPTIDE INCLUDING A CYSTEINE RESIDUE

(75) Inventors: Jumpei Naito, Kawasaki (JP); Shuya Satoh, Yokohama (JP); Manabu Komatsu, Kawasaki (JP); Hiroyuki Hashimoto, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 1087 days.

(21) Appl. No.: 13/576,124

(22) PCT Filed: Mar. 28, 2011

(86) PCT No.: PCT/JP2011/058474
§ 371 (c)(1),
(2), (4) Date: Jul. 30, 2012

(87) PCT Pub. No.: WO2011/122692
PCT Pub. Date: Oct. 6, 2011

(65) Prior Publication Data
US 2012/0301968 A1    Nov. 29, 2012

(30) Foreign Application Priority Data

Mar. 30, 2010  (JP) ................................. 2010-077842
Mar. 24, 2011  (JP) ................................. 2011-065780

(51) Int. Cl.
*G01N 33/68*  (2006.01)
*H01J 49/00*  (2006.01)

(52) U.S. Cl.
CPC ........... *G01N 33/6851* (2013.01); *H01J 49/00* (2013.01); *Y10T 436/182* (2015.01)

(58) Field of Classification Search
None
See application file for complete search history.

(56) References Cited

U.S. PATENT DOCUMENTS

| 5,738,829 | A  | * | 4/1998 | Kempe ......................... 422/107 |
| 6,287,806 | B1 |   | 9/2001 | Nishimura et al. |
| 7,446,309 | B2 |   | 11/2008 | Murayama et al. |
| 8,217,340 | B2 |   | 7/2012 | Yoshimura et al. |

(Continued)

FOREIGN PATENT DOCUMENTS

| EP | 2 112 680 A2 | 10/2009 |
| WO | 2004/050839 A2 | 6/2004 |
| WO | 2005/003715 A2 | 1/2005 |

OTHER PUBLICATIONS

Papayannopoulos, I. A. et al. "Amino acid sequence of a protease inhibitor isolated from Sarcophaga bullata determined by mass spectrometry," Protein Science (1992), 1, 278-288.*

(Continued)

*Primary Examiner* — Yelena G Gakh
*Assistant Examiner* — Michelle Adams
(74) *Attorney, Agent, or Firm* — Fitzpatrick, Cella, Harper & Scinto (57) ABSTRACT

The problem to be solved by the present invention is to provide a method for treating a polypeptide including a cysteine residue for enhancing the sensitivity of detection thereof in mass spectrometry using charged particles. A mass spectrometry method for a polypeptide including a cysteine residue is provided which includes treating the polypeptide including a cysteine residue with a cyanation agent, treating the cyanated polypeptide with a base, and then desorption ionizing the base-treated polypeptides using charged particles for mass spectrometry.

10 Claims, 5 Drawing Sheets

(56) References Cited

U.S. PATENT DOCUMENTS

2006/0118711 A1   6/2006  Murayama et al.
2008/0278706 A1*  11/2008 Murayama et al. ............ 356/36

OTHER PUBLICATIONS

Benninghoven, A., et al. "Peptide Analysis by Time-of-flight Secondary Ion Mass Spectrometry." Methods in Protein Sequence Analysis. Springer Berlin Heidelberg, 1989. 199-205.*

Lee, Terry D. "Fast Atom Bombardment and Secondary Ion Mass Spectrometry of Peptides and Proteins." Methods of Protein Microcharacterization (1986): 403-441.*

Jiang Wu et al., "A Novel Methodology for Assignment of Disulfide Bond Pairings in Proteins," 6 Protein Sci. 391-398 (1997) (XP002714576).

Gary D. Pipes et al., "Optimization and Applications of CDAP Labeling for the Assignment of Cysteines," 22(7) Pharm. Res. 1059-1068 (Jul. 2005) (XP019370888).

Régis Daniel et al., "Mass Spectrometric Determination of the Cleavage Sites in *Escherichia coli* Dihydroorotase Induced by a Cysteine-specific Reagent," 272(43) J. Biol. Chem. 26934-26939 (Oct. 1997) (XP055082987).

Extended European Search Report in European Application No. 11762912.1 (dated Oct. 29, 2013).

Hsin-Yao Tang et al., "Identification of alternative products and optimization of 2-nitro-5-thiocyanatobenzoic acid cyanylation and cleavage at cysteine residues," 334 Anal. Biochem. 48-61 (2004).

Jiang Wu et al., "A Srategy to Locate Cysteine Residues in Proteins by Specific Chemical Cleavage Followed by Matrix-Assisted Laser Desorption/Ionization Time-of-Flight Mass Spectrometry," 235 Anal. Biochem. 161-174 (1996).

* cited by examiner

MASS SPECTROMETRY METHOD FOR A POLYPEPTIDE INCLUDING A CYSTEINE RESIDUE

TECHNICAL FIELD

The present invention relates to a mass spectrometry method for a protein, a peptide, or a peptide obtained by digestion with an enzyme or the like (hereinafter referred to generally as a polypeptide).

BACKGROUND ART

After completion of decoding of the human genome sequence, attention has been drawn to proteome analysis in which proteins in actual charge of life phenomena are analyzed. This is because the direct analysis of a protein probably leads to the determination of the cause of disease, the development of new drugs, and tailor-made medicine. For example, a specific polypeptide called a marker protein is known to be selectively expressed on a certain type of diseased cells; the detection of the marker protein with high sensitivity is an important technology leading to the early detection of disease or the like.

Other reasons why the proteome analysis has received attention include the facts that the expression of a protein has proved to be incapable of being well predicted by the expression analysis of RNA as a transcript, i.e. transcriptome analysis, and that it is difficult to obtain the modified site and three-dimensional structure of a protein modified after translation from genomic information.

Mass spectrometry is widely used for proteome analysis because it can measure a polypeptide with high sensitivity and high resolution. Particularly, a matrix assisted laser desorption/ionization mass spectrometry method (MALDI-MS) can detect a peptide with a high mass number and hence is effectively used.

In recent years, attention has been given to measurement using a secondary ion mass spectrometry method (SIMS), which is a mass spectrometry method having high spatial resolution and reproducibility.

CITATION LIST

Patent Literature

PTL 1: U.S. Pat. No. 7,446,309
PTL 2: U.S. Pat. No. 6,287,806

Non Patent Literature

NPL 1: W. Speicher, et al., Anal. Biochem. 2004, 334, 48.

SUMMARY OF INVENTION

Technical Problem

An object of the present invention is to detect a polypeptide including cysteine with higher sensitivity than before by SIMS.

The present inventors have previously carried out intensive studies for the purpose of increasing the sensitivity of SIMS measurement and have hitherto found a "SIMS-specific sensitizing substance" which enhances sensitivity in detecting a peptide by SIMS (PTL 1). According to PTL 1, the inventors succeeded in detecting a single polypeptide with an m/z of up to about 6,000 and a peptide mixture with an m/z of up to about 1,600 by modifying the polypeptide(s), i.e., proton-modifying the polypeptide(s) using an acid having a pH of 6 or less, to enhance the signal intensity of SIMS. The present inventors also proposed a method for the highly sensitive detection of enzyme-digested polypeptides and a trace bio-related substance by SIMS using the above-described sensitizing substance.

The treatment of a polypeptide including cysteine with NTCB (2-nitro-5-thiocyano benzoic acid) is described in NPL 1. In NPL 1, a polypeptide is treated with NTCB and a base for digestion to analyze the digested polypeptide by MALDI-MS and an electrospray ionization mass spectrometry (ESI-MS). However, according to this literature, the treatment using NTCB and a base has been purely conducted to fragment a polypeptide to reduce the mass thereof, and is not intended to increase sensitivity in mass spectrometry by introducing a modification such as a 2-iminothiazolidine-4-carboxyl group into the site of the cysteine residue. In addition, the measurement has been conducted only by MALDI-MS and ESI-MS and not performed by SIMS.

PTL 2 discloses a method for producing a polypeptide using NTCB. This literature is intended to obtain a polypeptide including no cysteine residue and describes that a polypeptide including one cysteine residue is cleaved at the site of the cysteine residue by treatment with NTCB or the like. However, PTL 2 describes that the polypeptide including one cysteine residue is digested using NTCB, followed by partitioning the resultant two polypeptides using liquid chromatography (LC) and analyzing the polypeptide including no cysteine residue by SIMS. PTL 2 also does not suggest in any manner that the treatment with NTCB increases sensitivity in SIMS. Thus, NPL 1 and PTL 2 do not suggest the "SIMS-specific" peptide signal sensitizing effect of the present invention.

According to Patent document 1, the detection sensitivity was increased for a peptide with a m/z of 1,600 or less. For the proteome analysis, a polypeptide with a mass number of about 500 to 4,000 is desirably detected by mass spectrometry; the increased sensitivity of SIMS measurement in a higher mass number region has been demanded.

Solution to Problem

The present inventors have subjected a polypeptide including a cysteine residue to treatment with a cyanation agent and further treatment with a base. These treatments have provided a treated polypeptide in which the site of the cysteine residue is modified into a 2-iminothiazolidine-4-carboxyl group. The present inventors have found that the signal of the treated polypeptide can be detected even in a region in which the SIMS measurement has conventionally been incapable of detection (mass number: 1,600 or more), thereby accomplishing the present invention.

The present inventors have also found that the polypeptide including a cysteine residue can be digested while partially retaining the positional information of the polypeptide on a gold-deposited silicon substrate in the base treatment step of the above treatment steps by exposure to base vapor, immersion in a base-containing solution, addition of a base solution in a micro droplet, or treatment with a combination of a deliquescent material and a base vapor, thereby accomplishing the present invention.

Thus, the feature of the present invention relates to a mass spectrometry method for a polypeptide including a cysteine residue, comprising the steps of: cyanating the polypeptide with a cyanation agent; treating the cyanated polypeptide with a base; desorption ionizing the base-treated polypeptides using charged particles; and analyzing the desorption-ionized treated polypeptides by a mass spectrometry method.

Further features of the present invention will become apparent from the following description of exemplary embodiments with reference to the attached drawings.

DESCRIPTION OF EMBODIMENTS

The intended substance of the present invention is a polypeptide including a cysteine residue. The polypeptide is sometimes abbreviated as a "subject matter" in the present specification.

Figure 1:
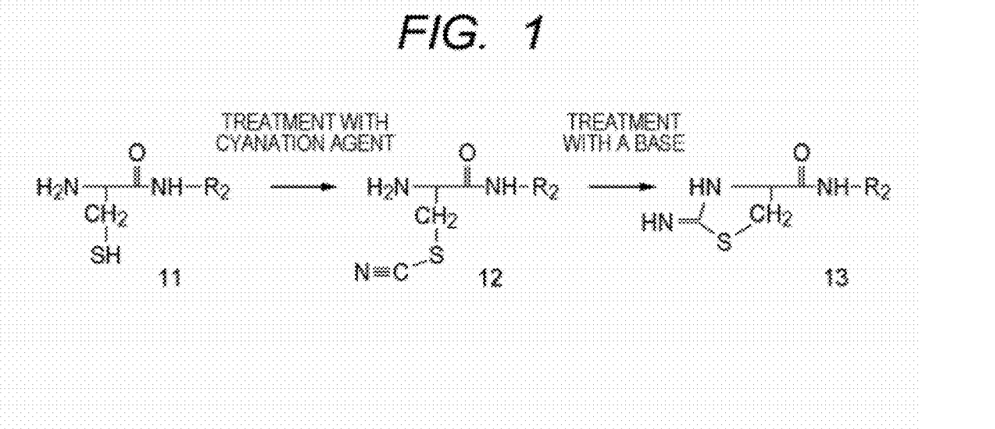
FIG. 1 is a series of reaction formulae indicating chemical structural changes by the treatment according to the present invention.

According to the present invention, the subject matter is treated with a cyanation agent and further with a base to provide a treated polypeptide (FIG. 1). In the treated polypeptide, the site of a cysteine residue is modified into a 2-iminothiazolidine-4-carboxyl group. When the subject matter includes the cysteine residue in a site other than the end thereof, it is cleaved at the site of the cysteine residue when treated with the base. In the present specification, all of the products obtained by the treatment of the subject matter with a cyanation agent and a base are each referred to as a treated polypeptide, in which both the above-described cleaved polypeptide and the non-cleaved polypeptide are included.

The treated polypeptide is detected with high signal intensity in SIMS compared to the non-treated polypeptide. As a result, the signal of the treated polypeptide can be detected even in a region of a mass number of 1,600 or more in which the SIMS measurement has conventionally been incapable of detection. Particularly, the treated polypeptide with a mass number of up to about 2,800 can be detected with a sufficient intensity. Thus, for example, the application of the method of the present invention to proteome analysis greatly enhances the accuracy of protein identification.

The enhancement of the signal intensity of the treated polypeptide is notably observed particularly in SIMS and such an effect is not obtained in other ionization such as MALDI-MS. A mechanism by which the signal intensity of the treated polypeptide is enhanced in SIMS has not fully been elucidated; however, the following two are dominant. (1) For a conventional method (PTL 1), when a polypeptide ion with a high mass number is sputtered, a charge is taken away by a surrounding substance immediately thereafter. In contrast, the treated polypeptide of the present invention has an easily protonated cyclic structure at the N-terminus and a charge is less easily taken away by a surrounding substance after sputtering. (2) The treated polypeptide of the present invention loses the thiol group of the cysteine residue compared to the polypeptide before treatment. This weakens intermolecular hydrogen bonding and increases the efficiency of sputtering.

In addition, the present invention enables a protein expressed in a body tissue (a section) to be digested with the positional information thereof retained; this point is probably also effective in the use thereof in SIMS. In this view point, the method of the present invention is likely to be more effective than a method using an enzyme.

A mass spectrometry method for a polypeptide including a cysteine residue is provided which comprises the steps of:
(1) treating the polypeptide with a cyanation agent;
(2) treating the resultant with a base;
(3) desorption ionizing the polypeptides obtained by the treatments of the steps (1) and (2) (treated polypeptides) using charged particles; and
(4) analyzing the mass of the desorption-ionized treated polypeptides using a mass spectrometry method, and is characterized in that the polypeptide is treated in the order of (1) to (4).

The mass spectrometry method of the present invention may further comprise the step of (5) reducing the cysteine residue before the step (1), before the step (2), or before the step (3).

The charged particles are preferably monoatomic ions or cluster ions.

In addition, in one aspect of the present invention, the polypeptide including a cysteine residue is present in a solution, in a tissue section, on a protein tip, in a gel, or on a film.

The cyanation agent in the present invention is not particularly limited; however, it is preferably a solution including any of 2-nitro-5-thiocyano benzoic acid (NTCB), 1-cyano-4-dimethylaminopyridinium tetrafluoroborate (CDAP), 1-cyano-4-dimethylaminopyridium salt (DMAP-CN), and CN$^-$ ion.

The present invention also provides a method for treating a polypeptide including a cysteine residue for analysis using secondary ion mass spectrometry, comprising treating the polypeptide with a cyanation agent and further treating the resultant with a base.

The present invention further provides a method for treating a polypeptide including a cysteine residue for analysis using secondary ion mass spectrometry, comprising modifying the cysteine residue with a 2-iminothiazolidine-4-carboxyl group.

Mass Spectrometer

The mass spectrometer used in the mass spectrometry method of the present invention is intended to irradiate a sample with a charged particle as a primary beam for desorption ionization to provide the mass information of a secondary ion produced by sputtering. Examples of the charged particle used as an ion source include a monoatomic ion beam and a cluster ion beam. In addition, the primary ion beam pulse frequency preferably ranges from 1 kHz to 50 kHz, and the primary ion beam energy preferably ranges from 12 keV to 25 keV. Further, the primary ion beam pulse width preferably ranges 0.5 ns to 10 ns. The mass measurement is made in the analyzer of a mass spectrometer. The analyzer is not limited in any manner; examples thereof which may be used include time-of-flight type, magnetic deflection type, quadrupole type, ion trap type and tandem type analyzers. The analyzer is properly selected depending on the compatibility with the above ion source.

Intended Polypeptide

As described above, the subject matter in the present specification refers to a polypeptide including a cysteine residue. Subject matters may also include a polypeptide during treatment or a polypeptide treated. The subject matter may include one or more cysteine residues. The subject matter can also be treated which is present in a tissue section, on a protein tip, or even in a gel, as well as which is present in a solution. In addition, the subject matter can be treated which is present on a film to which it has been transferred.

Entire Treatment Procedure

According to the present invention, the treatment with a base needs to be carried out after the treatment with a cyanation agent. When reduction is necessary, it can be performed, for example, before the treatment with a cyanation agent, between the treatment with a cyanation agent and the treatment with a base, or after the treatment with a base. Each of the treatments will be described below in detail.

Method for Adding Treatment

According to the present invention, methods for adding a treatment (a reducing agent, a cyanation agent, or a basic agent) to a subject matter can include methods using electrospray and a micro droplet, such as using a pipette, an ink jet, an air brush, and the like. Examples thereof which may be used also include a method which involves direct addition by a vapor-deposition technique, direct addition (sprinkling) of a powder of the treatment under atmosphere pressure, or immersion a material (e.g., tissue section) including the subject matter in a treatment solution. A material section (e.g., tissue) including a subject matter can also be immersed in a treatment solution to add the treatment, followed by sectioning the resultant. The procedure of treatment with a base may use a gas phase-solid phase reaction or a liquid phase reaction; however, preferred is a gas phase-solid phase reaction in terms of the prevention of the escape of peptide fragments or a liquid phase reaction in terms of the reaction rate. When the step of treatment with a base is carried out in the liquid phase, it is more preferable to cause the treatment solution to include a poor solvent (e.g., alcohol) for a peptide in view of suppressing the diffusion of peptide components.

When the subject matter is dissolved in a solution, the treatment is preferably added using a pipette for treatment in a homogeneous system. On the other hand, when the subject matter is included in a body tissue, the treatment is preferably added by the immersion of a section of the tissue because it takes longer to cause the solution to permeate the tissue itself. When it is desired to treat the subject matter while retaining the positional information thereof, the addition using an ink jet, the addition using an air brush, and the addition of a treatment using a vapor are preferable. The reason is that the diffusion of the treatment added is suppressed. When it is desired for the digestion to be performed using a liquid phase reaction to increase the digestion speed, a deliquescent material can be added to the surface of a material including the subject matter, followed by exposing the subject matter to a water vapor including a base (hereinafter also referred to as a "base vapor". Similarly, a solution including a base may be referred to as a "base solution") for digestion in a small amount of solution. The method therefor may be any method in which a small amount of solution can be held on the substrate (e.g., condensation due to temperature difference or placement of a water feeder in an incubator). Of the above methods for adding a treatment, a plurality of methods can also be combined to add a reducing agent, a cyanation agent, and a basic agent.

Reduction Treatment

The step of reducing a cysteine residue according to the present invention is a step for rendering some or all of a non-reduced state of cysteine residues of a subject matter or a treated polypeptide into a free state. When the cystein residue in the subject matter is in a free state, reduction is not necessary. The reducing agent can be added by the above method for adding a treatment. After adding the reducing agent, the subject matter during treatment needs to be incubated at a temperature of 20 to 60° C. The treatment time is not particularly limited; however, it is preferably short (less than 60 minutes) in view of the stability of the subject matter during treatment. When the subject matter is included in a tissue section or the like, the drying of the subject matter during treatment needs to be avoided; thus, it is preferably treated under moisturizing conditions. The pH of the solution including the subject matter during treatment is not particularly limited; however, it needs to be a pH at which the subject matter during treatment can be stably present. The pH of the solution including the subject matter during treatment is preferably 4 to 10 (both inclusive).

Cyanation Agent

The cyanation agent used for the present invention is not particularly limited; however, it preferably uses 2-nitro-5-thiocyano benzoic acid (NTCB), 1-cyano-4-dimethylaminopyridinium tetrafluoroborate (CDAP), or 1-cyano-4-dimethylaminopyridium salt (DMAP-CN) in view of safety. The cyanation agent is added by the above-described method for adding a treatment. After adding the cyanation agent, the subject matter during treatment needs to be incubated at a temperature of 20° C. or higher for the purpose of reaction. The treatment time is not particularly limited; however, it is preferably short (less than 60 minutes) in view of the stability of the subject matter during treatment. When the subject matter is included in a tissue section or the like, the drying of the subject matter during treatment needs to be avoided; thus, it is preferably treated under moisturizing conditions. The pH of the solution including the subject matter during treatment is preferably 7 to 8.5 (both inclusive).

Base

The base used for the present invention is not particularly limited; however, it is preferably one not adversely affecting subsequent mass spectrometry. A volatile base such as ammonia is particularly preferable because it can be added using a vapor and removed by drying after treatment. The base is added by the method for adding a treatment. After adding the base, the subject matter during treatment needs to be incubated at a temperature of 30 to 100° C. for the purpose of reaction. The treatment time is not particularly limited; however, it is preferably short (less than 2 hours) in terms of throughput. When the subject matter is included in a tissue section or the like, the drying of the subject matter during treatment needs to be avoided; thus, it is preferably treated under moisturizing conditions. The pH of the solution including the subject matter during treatment is preferably 8 to 10 (both inclusive).

The present invention will be more specifically described below with reference to Examples. The following specific examples are only illustrative of the best embodiments according to the present invention; however, the present invention is not intended to be limited to these specific embodiments.

EXAMPLES

Example 1

A polypeptide (CKVASLRETYGDMAD) (purchased from SIGMA Co. Ltd.)/ammonium hydrogen carbonate buffer (25 mM, pH 8.5) solution (0.5 mg/mL) was prepared. To 200 μL of the solution was added 20 μL of a dithiothreitol (DTT) solution (50 mM), which was then incubated at 60° C. for one hour (sample 1).

Thereafter, 80 μL of a 2-nitro-5-thiocyano benzoic acid (NTCB) solution (25 mM, pH 7.5) was added to the sample 1, which was then incubated at 40° C. for one hour. Subsequently, the solution was adjusted to a pH of 8.5 with aqueous ammonia (3%) and incubated at 50° C. for one hour (sample 2).

On to a gold-deposited silicon substrate were dropwise added 0.5 μL each of the sample 1 and the sample 2, which was then dried and subjected to SIMS measurement. The mass number of the polypeptide before treatment can be calculated to be 1658.8 and the mass number of the polypeptide after treatment, to be 1683.8.

Figure 2A:
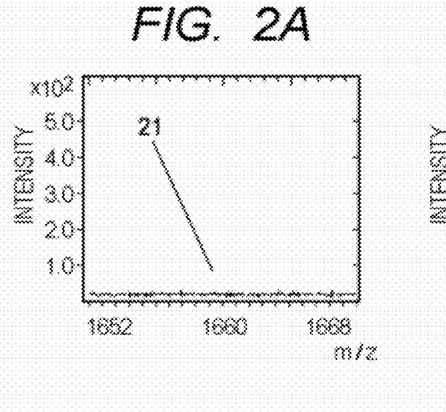
FIG. 2A is an SIMS spectrum of a synthetic polypeptide (CKVASLRETYGDMAD) before treatment.
Figure 2B:
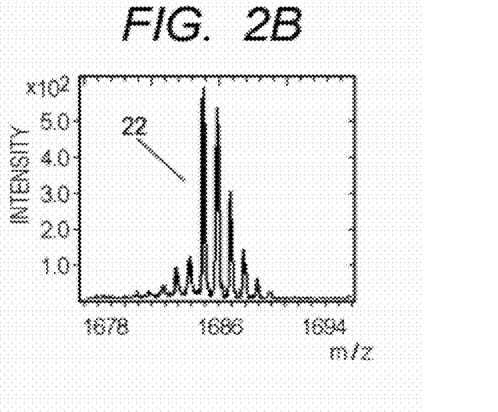
FIG. 2B is an SIMS spectrum of a synthetic polypeptide (CKVASLRETYGDMAD) after treatment.

Measurement conditions for SIMS were as follows:
Primary ion for measurement: $Bi_3^+$, 25 kV 0.3 pA [pulse current value]
Scanning: Sawtooth scan mode, 500×500 μm²
Pulse frequency of primary ion for measurement and cluster ion: 3.3 kHz
Pulse width of primary ion for measurement: about 0.8 ns
Beam diameter of primary ion for measurement: about 2 μm
Integration time: about 500 seconds The spectra resulting from the above measurements are shown in FIGS. 2A and 2B. No polypeptide signal was detected from the instillation of the sample 1 (21 in FIG. 2A), while the signals of treated polypeptides from the synthetic polypeptide could be detected from the instillation of the sample 2 (22 in FIG. 2B). This indicates that the treatment of the present invention increased the polypeptide signal.

Comparative Example 1

Figure 3:
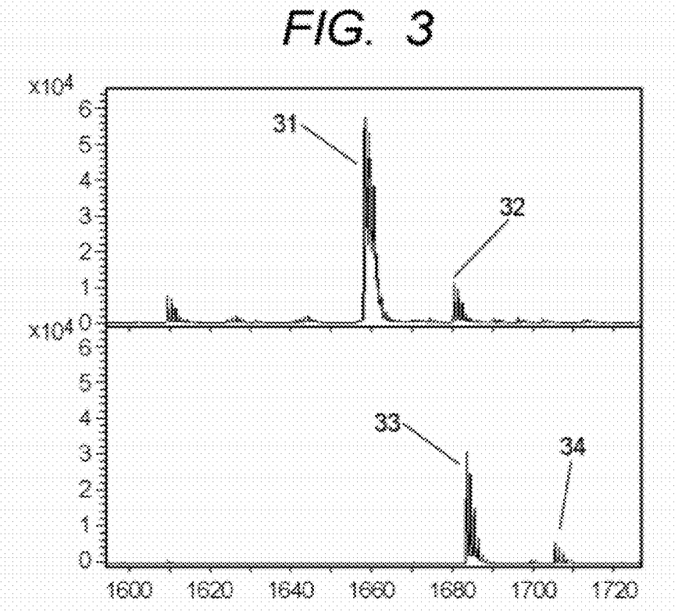
FIG. 3 is a set of spectra in the MALDI measurement of a synthetic polypeptide (CKVASLRETYGDMAD) before and after treatment.

The samples 1 and 2 prepared in Example 1 were each mixed with a 50 mM DHB/(0.1% TFA, acetonitrile) solution at a ratio of 1:1, which was then added dropwise to a substrate for MALDI measurement and measured for MALDI. As a result, the signals of the synthetic peptide and treated synthetic peptide were detected from each of the samples 1 and 2 (31, 32, 33, and 34 in FIG. 3). The intensities of the signals were comparable between both peptides; a signal-enhancing effect as seen for SIMS in Example 1 was not observed. This shows that the enhancing effect of the present invention is specific for SIMS.

Example 2

Figure 4A:
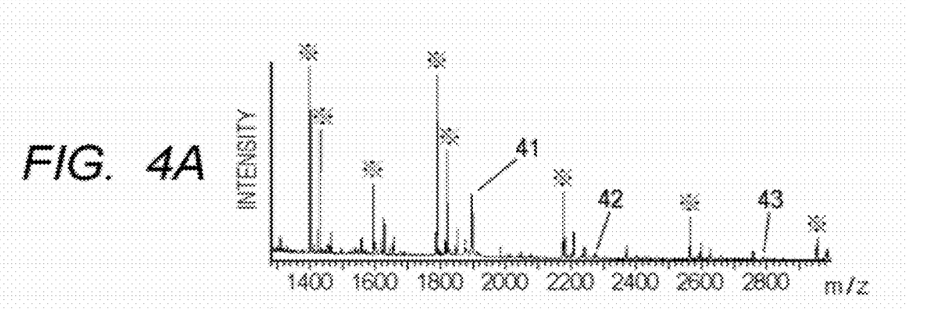
FIG. 4A is an SIMS spectrum of digested products of bovine serum albumin obtained by the digestion (treatment) based on the method of the present invention.

A bovine serum albumin/ammonium hydrogen carbonate buffer (25 mM, pH 8.5) solution (0.5 mg/mL) was prepared. The resultant bovine serum albumin solution was subjected to reduction, cyanation and base treatment in the same way as in Example 1 and then subjected to SIMS measurement under the same conditions as those in Example 1. As a result, a plurality of signals of digested polypeptides (treated and not-treated) or peptide stubs were detected in a region of a mass number of 1,600 to 2,800 (41, 42, and 43 in FIG. 4A).
* indicates a signal derived from gold.

Example 3

Figure 4B:
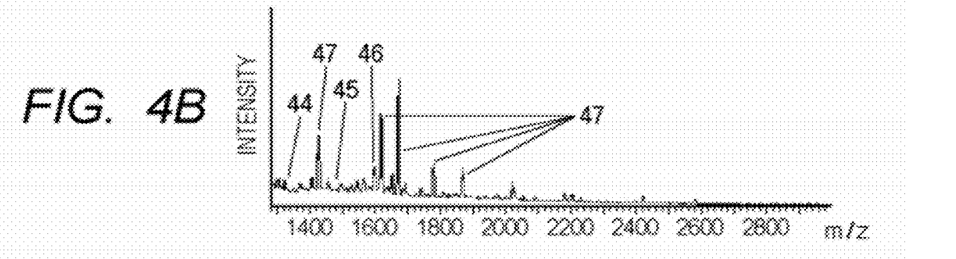
FIG. 4B is an SIMS spectrum of digested products of bovine serum albumin obtained by the digestion using trypsin.

A solution (200 μL) of 0.5 mg/mL of bovine serum albumin in ammonium hydrogen carbonate buffer (25 mM, pH 8.5) was prepared. To the resultant bovine serum albumin solution was added 1 μL of a 1 mg/mL trypsin solution, which was then incubated at 37° C. overnight. The solution was subjected to SIMS measurement under the same conditions as those in Example 2. As a result, signals of digested polypeptides were detected in a region of a mass number of about 1,600 (44, 45, and 46 in FIG. 4B). The signals 47 seem to be derived from contaminants (lipid and polypeptide digestion products).

In Example 2, polypeptides in a higher-mass region (mass number: 1,600 to 2,800) than that in Example 3 could be detected. Although a firm assertion cannot be made because of the difference in the amino acid sequence of the polypeptides detected, it is probably due to the signal of SIMS increased by the modification of the cysteine residue site of the present invention that the polypeptides in the higher-mass region could be detected in Example 2.

Example 4

An insulin/ammonium hydrogen carbonate buffer (25 mM, pH 8.5) solution ($6.66 \times 10^{-5}$ M) was prepared. The solution was subjected to reduction and cyanation in the same way as for the sample 2 of Example 1. The resultant solution was printed on a gold-deposited silicon substrate using Pulse Injecter from Cluster Technology Co., Ltd. and then dried.

Figure 5A:
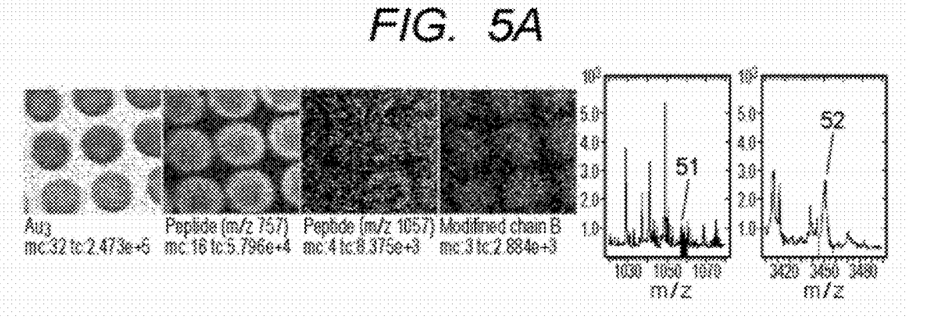
FIG. 5A is a set of SIMS data of insulin before and after the treatment of Example 4.
Figure 5B:
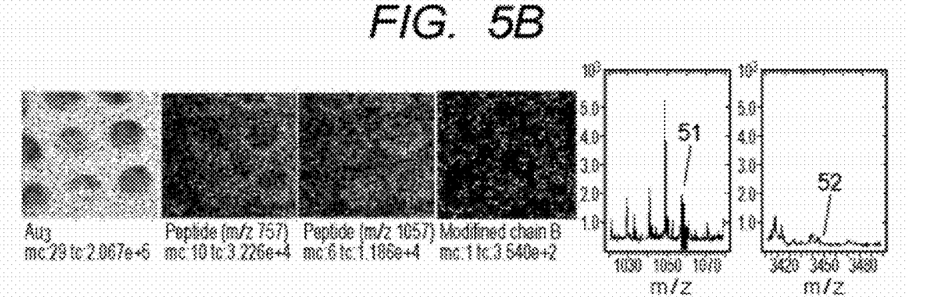
FIG. 5B is a set of SIMS data of insulin before and after the treatment of Example 4.

Printing conditions were as follows.
Blast nozzle diameter: 15 μm
Dot pitch: 200 μm
Liquid volume per spot 1.0 μL
Spot diameter: about 100 μm
Drive voltage: 7 V
Drive cycle: 200 Hz The SIMS data of the substrate thus prepared are shown in FIG. 5A. The substrate was also hermetically sealed together with a 28% aqueous ammonia/ethanol mixed solvent (1% of aqueous ammonia and 99% of ethanol), which was then incubated at 75° C. for 16 hours for base treatment. The substrate was subjected to SIMS treatment under the same conditions as those in Example 1. The results are shown in FIG. 5B. After base treatment, the signal of the insulin B chain as a treated product disappeared (52 in FIGS. 5A and 5B). Some peptides also showed enhanced signal intensities (e.g., m/z: 1057.41, 51 in FIGS. 5A and 5B). This seems to be because the base treatment caused the NTCB digestion to proceed.

Example 5

Figure 5C:
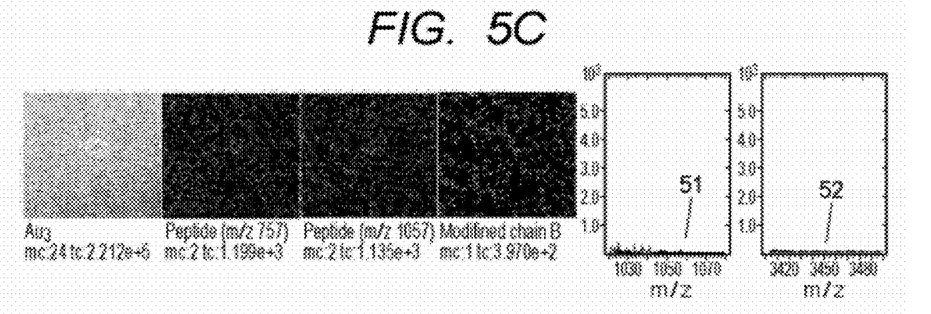
FIG. 5C is a set of SIMS data of insulin before and after the treatment of Example 5.

A printed gold-deposited silicon substrate was prepared by a method identical to that in Example 4. Aqueous ammonia having a pH of 9 was added dropwise to the gold-deposited silicon substrate for base treatment, followed by SIMS measurement. As a result, some signals corresponding to theoretical fragments were detected, but positional information on the substrate was little retained because of the increased escape of components (FIG. 5C). When FIG. 5B in which the base treatment was performed using ammonia vapor was compared with FIG. 5C in which the base treatment was carried out using droplets thereof, the images from $Au_3$, Peptide (m/z 757) and Peptide (m/z 1057.41) showed that the positional information was retained in FIG. 5B. This seems to be because digestion in ammonia vapor (or a small amount of water deposited on the substrate by the ammonia vapor and condensation) could suppress the escape of components.

Example 6

Figure 6A:
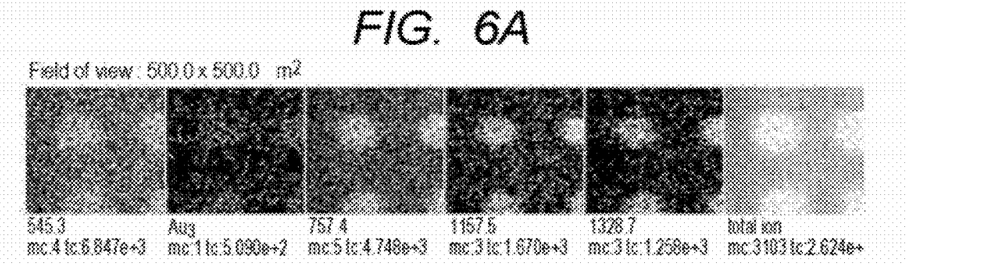
FIG. 6A is a set of SIMS images of insulin after the treatment of Example 6.
Figure 6B:
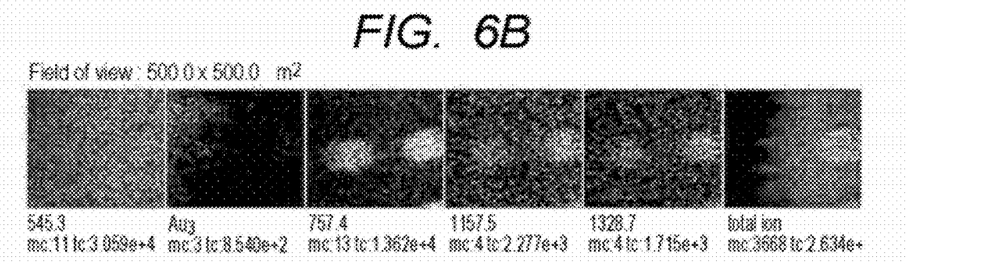
FIG. 6B is a set of SIMS images of insulin after the treatment of Example 6.
Figure 6C:
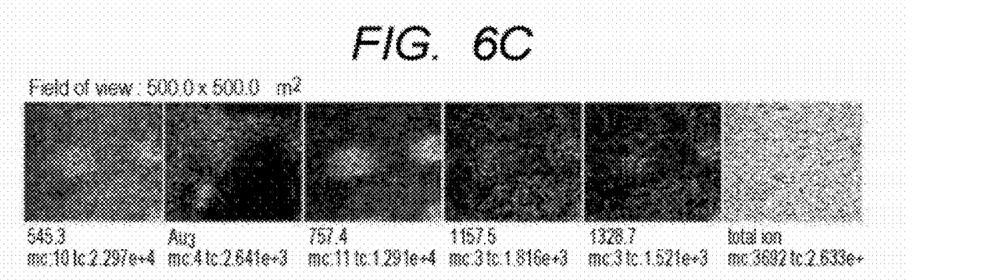
FIG. 6C is a set of SIMS images of insulin after the treatment of Example 6.
Figure 6D:
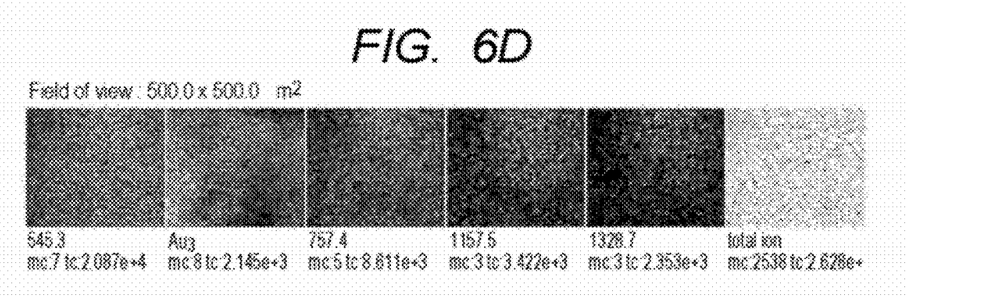
FIG. 6D is a set of SIMS images of insulin after the treatment of Example 6.

An insulin/ammonium hydrogen carbonate buffer (25 mM, pH 8.5) solution ($6.66 \times 10^{-5}$ M) was prepared. The solution was subjected to reduction, cyanation and base treatment in the same way as for the sample 2 of Example 1. This solution was printed on a gold-deposited silicon substrate in the same way as in Example 4. SIMS images from the substrate are shown in FIG. 6A. They are a peptide with an m/z of 545, $Au_3$, a peptide with an m/z of 757, a peptide with an m/z of 1,157, a peptide with an m/z of 1,328, and total ion, respectively from the left. To the substrate was added dropwise 5 μL of butanol, ethanol, or distilled water, which was then dried as it was. SIMS images after drying are shown in FIGS. 6B, 6C and 6D, respectively. Insulin on the gold-deposited silicon substrate to which butanol was added dropwise substantially maintained a dot pattern of Ink Jet (IJ) (FIG. 6B), whereas insulin on the gold-deposited silicon substrate to which distilled water was added dropwise maintained no dot pattern (FIG. 6D). Insulin on the gold-deposited silicon substrate to which ethanol was added dropwise showed results midway therebetween (FIG. 6C). Distilled water dissolves insulin. In contrast, butanol much less easily dissolves insulin; thus, the diffusion of insulin is suppressed, which seems to have led to such a result. Application of this result can result in the digestion of a peptide for which the diffusion of its components is suppressed.

Example 7

A sample-printed gold-deposited silicon substrate was prepared in the same way as in Example 4. The substrate was immersed in an ammonia/ethanol solution (1% of 28% aqueous ammonia and 99% of ethanol), which was then incubated at 37° C. for 8 hours. Thereafter, the substrate was taken out, dried and subjected to SIMS measurement. As a result, peptide components remained to some extent on the substrate, and signals were observed at positions corresponding to insulin fragments (m/z: 545.3 and 1132.5) in SIMS.

Example 8

A printed gold-deposited silicon substrate was prepared by a method identical to that in Example 4. The gold-deposited silicon substrate was immersed in aqueous ammonia having a pH of 9, which was then incubated at 37° C. for 8 hours. Thereafter, the substrate was taken out, dried and subjected to SIMS measurement. As a result, positional information was lost, and almost no peptide signal could be detected. In Example 7, because ethanol, which less easily dissolves a peptide, was added in a large amount, the flowing-out of peptide components on the substrate was suppressed, which probably enabled the detection of peptides.

Example 9

Figure 7A:
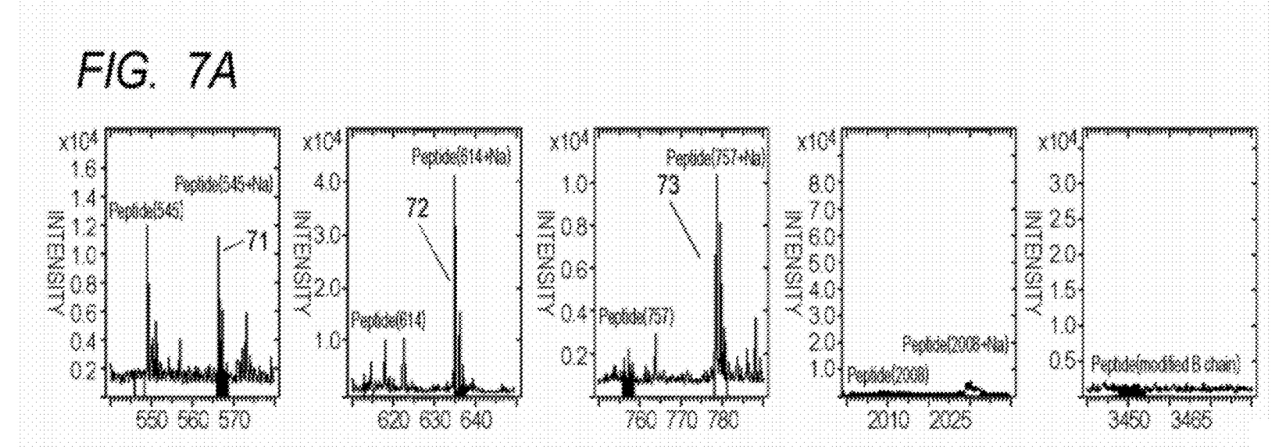
FIG. 7A is a set of SIMS spectra of insulin after the treatment of Examples 9 and 10.

An insulin/ammonium hydrogen carbonate buffer (25 mM, pH 8.5) solution ($6.66 \times 10^{-5}$ M) was prepared. The solution was subjected to reduction and cyanation in the same way as for the sample 2 of Example 1, and NaCl was then added thereto to adjust the resultant solution such that it is a 0.1% NaCl solution. The solution was printed on a gold-deposited silicon substrate under the same conditions as those in Example 3, and dried. The gold-deposited silicon substrate was hermetically sealed together with 1% aqueous ammonia, which was then incubated at 37° C. for 8 hours. In the SIMS data of the substrate, SIMS signals of digested products of insulin, 71, 72 and 73, were obtained as shown in FIG. 7A. The images of the resultant insulin fragments each maintained a dot pattern of IJ.

Example 10

Figure 7B:
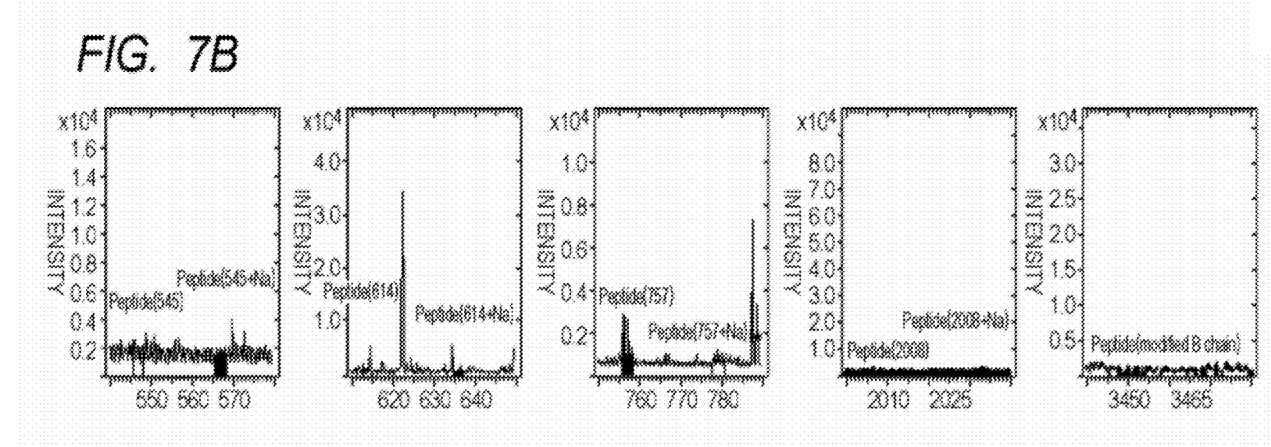
FIG. 7B is a set of SIMS spectra of insulin after the treatment of Examples 9 and 10.

The same printed gold-deposited silicon substrate as that prepared in Example 4 was incubated in the same way as in Example 9. As a result, a dot pattern of IJ was maintained, but no insulin fragment was detected (FIG. 7B). Whereas treated products of insulin was present in the solid phase in this Example, treated products of insulin was present in the solution in Example 9 since the addition of NaCl enabled the maintenance of a small amount of water on the substrate. Consequently, this Comparative Example represents a gas phase-solid phase reaction, while Example 9 represents a liquid phase reaction. This probably caused the digestion to proceed in Example 9.

REFERENCE SIGNS LIST

11 Chemical Structure of Subject Matter
12 Chemical Structure of Subject Matter after Treatment with Cyanation Agent
13 Chemical Structure of Treated Polypeptide from Subject Matter
21 SIMS Signal (m/z: 1658.8) of Polypeptide (CKVASLRETYGDMAD)
22 SIMS Signal (m/z: 1683.8) of Treated Polypeptide from Polypeptide (CKVASLRETYGDMAD)
31 MALDI Signal (m/z: 1658.8) of Polypeptide (CKVASLRETYGDMAD)
32 MALDI Signal (m/z: 1681.9) of Polypeptide (CKVASLRETYGDMAD) Sodium Adduct
33 MALDI Signal (m/z: 1683.8) of Treated Polypeptide from Polypeptide (CKVASLRETYGDMAD)
34 MALDI Signal (m/z: 1706.8) of Treated Polypeptide Sodium Adduct from Polypeptide (CKVASLRETYGDMAD)
41 SIMS Signal (m/z: 1881.0) of Digested Product of Bovine Serum Albumin
42 SIMS Signal (m/z: 2266.0) of Digested Product of Bovine Serum Albumin 43 SIMS Signal (m/z: 2778.3) of Digested Product of Bovine Serum Albumin
44 SIMS Signal (m/z: 1305.7) of Digested Product of Bovine Serum Albumin
45 SIMS Signal (m/z: 1479.8) of Digested Product of Bovine Serum Albumin
46 SIMS Signal (m/z: 1567.8) of Digested Product of Bovine Serum Albumin
47 Signals of Potential Contaminants (Lipid, Polypeptide Digestion Product)
51 SIMS Signal (m/z: 1057.41) of Peptide as a Likely Insulin Fragment
52 SIMS Signal (m/z: 3450.68) of Treated Insulin B Chain
71 SIMS Signal (m/z: 567.3) of Digested Product of Insulin
72 SIMS Signal (m/z: 636.3) of Digested Product of Insulin
73 SIMS Signal (m/z: 779.4) of Digested Product of Insulin While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2010-077842, filed Mar. 30, 2010, and No. 2011-065780 filed Mar. 24, 2011 which are hereby incorporated by reference herein in their entirety.

The invention claimed is:

1. A mass spectrometry method for a polypeptide including a cysteine residue, comprising:
   cyanating the polypeptide with a cyanation agent;
   treating the cyanated polypeptide with a base;
   desorption ionizing the base-treated polypeptide using charged particles to analyze a mass of the desorption-ionized treated polypeptide by using a secondary ion mass spectrometry method,
   wherein the treating of the cyanated polypeptide with the base comprises adding a deliquescent material to the cyanated polypeptide and further feeding water and the base using base vapor.

2. The mass spectrometry method according to claim 1, wherein the base-treated polypeptide is reduced at the cysteine residue thereof prior to the desorption ionizing.

3. The mass spectrometry method according to claim 1, wherein the treating of the cyanated polypeptide with the base further comprises immersing the cyanated polypeptide in a base solution.

4. The mass spectrometry method according to claim 1, wherein the treating of the cyanated polypeptide with the base further comprises adding the base to the cyanated polypeptide using an electrospray or as a micro droplet.

5. The mass spectrometry method according to claim 1, wherein the charged particles are one of monoatomic ions and cluster ions.

6. The mass spectrometry method according to claim 1, wherein the polypeptide including the cysteine residue is present in a solution, in a tissue section, on a protein tip, in a gel, or on a film.

7. The mass spectrometry method according to claim 1, wherein the cyanation agent is a solution including one of 2-nitro-5-thiocyanobenzoic acid (NTCB), 1-cyano-4-dimethylaminopyridinium tetrafluoroborate (CDAP), 1-cyano-4-dimethylaminopyridium salt (DMAP-CN), and a $CN^-$ ion.

8. The mass spectrometry method according to claim 1, wherein the desorption ionizing is performed without a matrix.

9. The mass spectrometry method according to claim 1, wherein the treating of the cyanated polypeptide with the base is performed so as to retain at least partially polypeptide positional information.

10. A mass spectrometry method for a polypeptide including a cysteine residue, the method comprising:
    cyanating the polypeptide with a cyanation agent;
    treating the cyanated polypeptide with a base;
    desorption ionizing the base-treated polypeptide using charged particles to analyze a mass of the desorption-ionized treated polypeptide by using a secondary ion mass spectrometry method,
    wherein the treating of the cyanated polypeptide with the base comprises adding deliquescent NaCl to the cyanated polypeptide and further feeding water and the base using base vapor.

* * * * *